United States Patent
Brown et al.

(10) Patent No.: US 9,000,066 B2
(45) Date of Patent: Apr. 7, 2015

(54) MULTI-MODAL SHAPE MEMORY POLYMERS

(75) Inventors: Malcolm Brown, Otley (GB); Horacio Montes De Oca Balderas, York (GB); Michael Hall, Middlesbrough (GB); John Rose, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 12/595,341

(22) PCT Filed: Apr. 18, 2008

(86) PCT No.: PCT/US2008/060783
§ 371 (c)(1),
(2), (4) Date: Oct. 9, 2009

(87) PCT Pub. No.: WO2008/131197
PCT Pub. Date: Oct. 30, 2008

(65) Prior Publication Data
US 2011/0144751 A1    Jun. 16, 2011

Related U.S. Application Data

(60) Provisional application No. 60/912,827, filed on Apr. 19, 2007.

(51) Int. Cl.
| | |
|---|---|
| *A61K 6/083* | (2006.01) |
| *C08L 33/08* | (2006.01) |
| *A61L 31/14* | (2006.01) |
| *A61L 31/04* | (2006.01) |
| *C08L 33/10* | (2006.01) |

(Continued)

(52) U.S. Cl.
CPC .............. *A61L 31/14* (2013.01); *A61L 31/04* (2013.01); *C08L 33/08* (2013.01); *C08L 33/10* (2013.01); *C08L 33/12* (2013.01); *C08L 35/06* (2013.01); *C08L 67/04* (2013.01); *A61L 2400/16* (2013.01); *C08G 2280/00* (2013.01); *C08L 25/04* (2013.01); *C08L 33/06* (2013.01)

(58) Field of Classification Search
USPC ........................................................ 424/426
See application file for complete search history.

(56) References Cited

U.S. PATENT DOCUMENTS

| | | |
|---|---|---|
| 3,531,561 A | 9/1970 | Trehu |
| 3,636,956 A | 1/1972 | Schneider |

(Continued)

FOREIGN PATENT DOCUMENTS

| | | |
|---|---|---|
| CA | 2254002 | 5/2000 |
| CN | 1857742 | 11/2006 |

(Continued)

OTHER PUBLICATIONS

Chart BMEN 343 Polymer Tg chart.*

(Continued)

*Primary Examiner* — James J Seidleck
*Assistant Examiner* — Peter A Salamon
(74) *Attorney, Agent, or Firm* — David L. Fox; JL Salazar Law Firm

(57) ABSTRACT

The present disclosure relates to a multi-modal shape memory polymer material comprising a blend of at least one polymer component having a first molecular weight and at least a second polymer component having a second molecular weight that is less than the first component.

13 Claims, 1 Drawing Sheet

(51) Int. Cl.
*C08L 33/12* (2006.01)
*C08L 35/06* (2006.01)
*C08L 67/04* (2006.01)
C08L 25/04 (2006.01)
C08L 33/06 (2006.01)

(56) References Cited

U.S. PATENT DOCUMENTS

| | | |
|---|---|---|
| 3,736,646 A | 6/1973 | Schmitt et al. |
| 3,797,499 A | 3/1974 | Schneider |
| 3,856,905 A | 12/1974 | Dawson |
| 3,926,459 A | 12/1975 | Pontigny |
| 4,137,921 A | 2/1979 | Okuzumi et al. |
| 4,181,983 A | 1/1980 | Kulkarni |
| 4,438,253 A | 3/1984 | Casey et al. |
| 4,523,591 A | 6/1985 | Kaplan et al. |
| 4,539,981 A | 9/1985 | Tung |
| 4,559,945 A | 12/1985 | Koelmel et al. |
| 4,636,215 A | 1/1987 | Schwartz |
| 4,700,704 A | 10/1987 | Jamiolkowski et al. |
| 4,756,307 A | 7/1988 | Crowninshield |
| 4,916,207 A | 4/1990 | Boyle, Jr. et al. |
| 4,938,763 A | 7/1990 | Dunn et al. |
| 4,950,258 A | 8/1990 | Kawai et al. |
| 4,968,317 A | 11/1990 | Tormala et al. |
| 4,990,161 A | 2/1991 | Kampner |
| 5,049,591 A | 9/1991 | Hayashi et al. |
| 5,053,035 A | 10/1991 | McLaren |
| 5,061,181 A | 10/1991 | Niznick |
| 5,108,289 A | 4/1992 | Fukuyo |
| 5,108,755 A | 4/1992 | Daniels et al. |
| 5,110,852 A | 5/1992 | Gogolewski et al. |
| 5,192,301 A | 3/1993 | Kamiya et al. |
| 5,201,771 A | 4/1993 | Belykh et al. |
| 5,208,305 A * | 5/1993 | Grootaert ............... 526/194 |
| 5,250,584 A | 10/1993 | Ikada et al. |
| 5,266,608 A | 11/1993 | Katz et al. |
| 5,275,601 A | 1/1994 | Gogolewski et al. |
| 5,294,395 A | 3/1994 | Broyer |
| 5,324,308 A | 6/1994 | Pierce |
| 5,333,624 A | 8/1994 | Tovey |
| 5,360,448 A | 11/1994 | Thramann |
| 5,364,400 A | 11/1994 | Rego, Jr. et al. |
| 5,376,120 A | 12/1994 | Sarver et al. |
| 5,383,931 A * | 1/1995 | Hehli et al. ............. 623/17.18 |
| 5,407,445 A | 4/1995 | Tautvydas et al. |
| 5,417,712 A | 5/1995 | Whittaker et al. |
| 5,437,918 A | 8/1995 | Taniguchi et al. |
| 5,441,515 A | 8/1995 | Khosravi et al. |
| 5,458,653 A | 10/1995 | Davidson |
| 5,470,334 A | 11/1995 | Ross et al. |
| 5,525,706 A | 6/1996 | Gruber et al. |
| 5,527,337 A | 6/1996 | Stack et al. |
| 5,527,341 A | 6/1996 | Gogolewski et al. |
| 5,562,704 A | 10/1996 | Tamminmaki et al. |
| 5,567,431 A | 10/1996 | Vert et al. |
| 5,569,250 A | 10/1996 | Sarver et al. |
| 5,571,193 A | 11/1996 | Kampner |
| 5,571,204 A | 11/1996 | Nies |
| 5,633,002 A | 5/1997 | Stricker et al. |
| 5,634,936 A | 6/1997 | Linden et al. |
| 5,641,502 A | 6/1997 | Skalla et al. |
| 5,660,846 A | 8/1997 | Cheikh |
| 5,665,831 A | 9/1997 | Neuenschwander et al. |
| 5,670,161 A | 9/1997 | Healy et al. |
| 5,676,699 A | 10/1997 | Gogolewski et al. |
| 5,690,671 A | 11/1997 | McGurk et al. |
| 5,695,497 A | 12/1997 | Stahelin |
| 5,700,901 A | 12/1997 | Hurst et al. |
| 5,716,410 A | 2/1998 | Wang et al. |
| 5,716,413 A | 2/1998 | Walter et al. |
| 5,733,330 A | 3/1998 | Cox |
| 5,741,329 A | 4/1998 | Agrawal et al. |
| 5,760,118 A | 6/1998 | Sinclair et al. |
| 5,766,239 A | 6/1998 | Cox |
| 5,766,618 A | 6/1998 | Laurencin et al. |
| 5,792,400 A | 8/1998 | Talja et al. |
| 5,817,328 A | 10/1998 | Gresser et al. |
| 5,834,582 A | 11/1998 | Sinclair et al. |
| 5,837,276 A | 11/1998 | Cheikh |
| 5,853,639 A | 12/1998 | Kawakami et al. |
| 5,863,297 A | 1/1999 | Walter et al. |
| 5,868,746 A | 2/1999 | Sarver et al. |
| 5,893,850 A | 4/1999 | Cachia |
| 5,902,599 A | 5/1999 | Anseth et al. |
| 5,904,658 A | 5/1999 | Niederauer et al. |
| 5,908,918 A | 6/1999 | Chen et al. |
| 5,935,172 A | 8/1999 | Ochoa et al. |
| 5,939,453 A | 8/1999 | Heller et al. |
| 5,947,893 A | 9/1999 | Agrawal et al. |
| 5,951,288 A | 9/1999 | Sawa |
| 5,968,092 A | 10/1999 | Buscemi et al. |
| 5,977,204 A | 11/1999 | Boyan et al. |
| 5,980,564 A | 11/1999 | Stinson |
| 5,997,580 A | 12/1999 | Mastrorio et al. |
| 5,997,582 A | 12/1999 | Weiss |
| 6,001,100 A | 12/1999 | Sherman et al. |
| 6,001,101 A | 12/1999 | Augagneur et al. |
| 6,005,161 A | 12/1999 | Brekke et al. |
| 6,071,982 A | 6/2000 | Wise et al. |
| 6,077,989 A | 6/2000 | Kandel et al. |
| 6,113,624 A | 9/2000 | Bezwada et al. |
| 6,136,369 A | 10/2000 | Leitao et al. |
| 6,150,497 A | 11/2000 | Sastry et al. |
| 6,156,842 A | 12/2000 | Hoenig et al. |
| 6,160,084 A | 12/2000 | Langer et al. |
| 6,162,225 A | 12/2000 | Gertzman et al. |
| 6,168,570 B1 | 1/2001 | Ferrera |
| 6,179,842 B1 | 1/2001 | Spotorno et al. |
| 6,203,573 B1 | 3/2001 | Walter et al. |
| 6,206,883 B1 | 3/2001 | Tunc |
| 6,248,108 B1 | 6/2001 | Tormala et al. |
| 6,248,430 B1 | 6/2001 | Toyoda et al. |
| 6,277,390 B1 | 8/2001 | Schaffner |
| 6,281,262 B1 * | 8/2001 | Shikinami ............... 523/105 |
| 6,283,973 B1 | 9/2001 | Hubbard et al. |
| 6,293,950 B1 | 9/2001 | Lynch et al. |
| 6,299,448 B1 | 10/2001 | Zdrahala et al. |
| 6,303,697 B1 | 10/2001 | Yuan et al. |
| 6,315,788 B1 | 11/2001 | Roby |
| 6,344,496 B1 | 2/2002 | Niederauer et al. |
| 6,375,465 B1 | 4/2002 | Engman et al. |
| 6,388,043 B1 | 5/2002 | Langer et al. |
| 6,406,498 B1 | 6/2002 | Tormala et al. |
| 6,425,923 B1 | 7/2002 | Stalcup et al. |
| 6,436,136 B1 | 8/2002 | Flodin et al. |
| 6,447,515 B1 | 9/2002 | Meldrum |
| 6,468,277 B1 | 10/2002 | Justin et al. |
| 6,486,296 B1 | 11/2002 | Shimamoto et al. |
| 6,488,938 B1 | 12/2002 | Ogura et al. |
| 6,503,278 B1 | 1/2003 | Pohjonen et al. |
| 6,508,830 B2 | 1/2003 | Steiner |
| 6,511,511 B1 | 1/2003 | Slivka et al. |
| 6,514,286 B1 | 2/2003 | Leatherbury et al. |
| 6,547,792 B1 | 4/2003 | Tsuji et al. |
| 6,565,606 B1 | 5/2003 | Bruce et al. |
| 6,579,533 B1 | 6/2003 | Tormala et al. |
| 6,583,232 B1 * | 6/2003 | Brown ..................... 525/410 |
| 6,599,323 B2 | 7/2003 | Melican et al. |
| 6,605,090 B1 | 8/2003 | Trieu et al. |
| 6,613,089 B1 | 9/2003 | Estes et al. |
| 6,623,487 B1 | 9/2003 | Goshert |
| 6,652,582 B1 | 11/2003 | Stinson |
| 6,716,957 B2 | 4/2004 | Tunc |
| 6,719,935 B2 | 4/2004 | Tunc |
| 6,720,402 B2 | 4/2004 | Langer et al. |
| 6,726,696 B1 | 4/2004 | Houser et al. |
| 6,758,862 B2 | 7/2004 | Berry et al. |
| 6,758,863 B2 | 7/2004 | Estes et al. |
| 6,783,712 B2 | 8/2004 | Slivka et al. |
| 6,827,743 B2 | 12/2004 | Eisenmann et al. |
| 6,830,575 B2 | 12/2004 | Stenzel et al. |
| 6,841,111 B2 | 1/2005 | Rickner et al. |
| 6,843,799 B2 | 1/2005 | Bartlett |

(56) References Cited

U.S. PATENT DOCUMENTS

| | | | |
|---|---|---|---|
| 6,852,825 B2 | 2/2005 | Lendlein et al. | |
| 6,869,445 B1 | 3/2005 | Johnson | |
| 6,881,766 B2 | 4/2005 | Hain | |
| 6,902,584 B2 | 6/2005 | Kwan et al. | |
| 6,908,466 B1 | 6/2005 | Bonutti et al. | |
| 6,908,624 B2* | 6/2005 | Hossainy et al. | 424/424 |
| 6,916,321 B2 | 7/2005 | TenHuisen et al. | |
| 6,951,956 B2* | 10/2005 | Yamane et al. | 562/587 |
| 6,974,862 B2 | 12/2005 | Ringeisen et al. | |
| 7,012,106 B2 | 3/2006 | Yuan et al. | |
| 7,033,603 B2 | 4/2006 | Nelson et al. | |
| 7,192,443 B2 | 3/2007 | Solem et al. | |
| 7,208,550 B2 | 4/2007 | Mather et al. | |
| 7,214,765 B2 | 5/2007 | Ringeisen et al. | |
| 7,261,716 B2 | 8/2007 | Strobel et al. | |
| 7,261,734 B2 | 8/2007 | Gellman et al. | |
| 7,268,205 B2 | 9/2007 | Williams et al. | |
| 7,270,813 B2 | 9/2007 | Shimp et al. | |
| 7,285,087 B2 | 10/2007 | Moaddeb et al. | |
| 7,285,130 B2 | 10/2007 | Austin | |
| 7,314,480 B2 | 1/2008 | Eidenschink et al. | |
| 7,335,375 B2 | 2/2008 | Li et al. | |
| 7,378,144 B2 | 5/2008 | DeMeo et al. | |
| 7,455,674 B2 | 11/2008 | Rose | |
| 7,524,891 B2 | 4/2009 | Rose | |
| 7,553,923 B2 | 6/2009 | Williams et al. | |
| 2001/0012940 A1 | 8/2001 | Tunc | |
| 2001/0018614 A1 | 8/2001 | Bianchi | |
| 2002/0022588 A1 | 2/2002 | Wilkie et al. | |
| 2002/0029041 A1 | 3/2002 | Hover et al. | |
| 2002/0029043 A1 | 3/2002 | Ahrens et al. | |
| 2002/0071822 A1 | 6/2002 | Uhrich | |
| 2002/0082362 A1 | 6/2002 | Brocchini et al. | |
| 2002/0120348 A1 | 8/2002 | Melican et al. | |
| 2002/0138154 A1 | 9/2002 | Li et al. | |
| 2002/0150775 A1 | 10/2002 | Ishikawa et al. | |
| 2002/0160032 A1 | 10/2002 | Long et al. | |
| 2003/0045941 A1 | 3/2003 | Lewallen | |
| 2003/0055198 A1 | 3/2003 | Langer et al. | |
| 2003/0104031 A1 | 6/2003 | Dumont et al. | |
| 2003/0114937 A1 | 6/2003 | Leatherbury et al. | |
| 2003/0120280 A1 | 6/2003 | Rolier et al. | |
| 2003/0125745 A1 | 7/2003 | Tseng et al. | |
| 2003/0130742 A1* | 7/2003 | Connelly et al. | 623/23.35 |
| 2003/0153971 A1 | 8/2003 | Chandrasekaran | |
| 2003/0153972 A1 | 8/2003 | Helmus | |
| 2003/0180344 A1 | 9/2003 | Wise et al. | |
| 2003/0236573 A1 | 12/2003 | Evans et al. | |
| 2004/0002770 A1 | 1/2004 | King et al. | |
| 2004/0015187 A1 | 1/2004 | Lendlein et al. | |
| 2004/0019386 A1 | 1/2004 | Ferree | |
| 2004/0030341 A1 | 2/2004 | Aeschlimann et al. | |
| 2004/0030342 A1 | 2/2004 | Trieu et al. | |
| 2004/0052992 A1 | 3/2004 | Boone et al. | |
| 2004/0054372 A1 | 3/2004 | Corden et al. | |
| 2004/0106734 A1 | 6/2004 | Rose | |
| 2004/0109823 A1 | 6/2004 | Kaplan | |
| 2004/0110285 A1 | 6/2004 | Lendlein et al. | |
| 2004/0115239 A1 | 6/2004 | Shastri et al. | |
| 2004/0131681 A1 | 7/2004 | Ambrose et al. | |
| 2004/0143221 A1 | 7/2004 | Shadduck | |
| 2004/0153075 A1 | 8/2004 | Roger | |
| 2004/0156878 A1 | 8/2004 | Rezania et al. | |
| 2004/0172118 A1 | 9/2004 | Gibson | |
| 2004/0193154 A1 | 9/2004 | Leatherbury et al. | |
| 2004/0241203 A1 | 12/2004 | Shakesheff et al. | |
| 2004/0242722 A1 | 12/2004 | Rose | |
| 2004/0254639 A1 | 12/2004 | Li et al. | |
| 2004/0258732 A1 | 12/2004 | Shikinami | |
| 2004/0259972 A1 | 12/2004 | Ringeisen et al. | |
| 2004/0260398 A1 | 12/2004 | Kelman | |
| 2004/0265385 A1 | 12/2004 | West | |
| 2004/0267263 A1 | 12/2004 | May | |
| 2005/0008672 A1 | 1/2005 | Winterbottom et al. | |
| 2005/0013793 A1 | 1/2005 | Beckman et al. | |
| 2005/0019404 A1 | 1/2005 | Sung et al. | |
| 2005/0033295 A1 | 2/2005 | Wisnewski | |
| 2005/0043751 A1 | 2/2005 | Phan et al. | |
| 2005/0043752 A1 | 2/2005 | Phan et al. | |
| 2005/0070928 A1 | 3/2005 | Heino et al. | |
| 2005/0080483 A1 | 4/2005 | Solem et al. | |
| 2005/0080489 A1 | 4/2005 | Estes et al. | |
| 2005/0085313 A1 | 4/2005 | Nishitani | |
| 2005/0085812 A1 | 4/2005 | Sherman et al. | |
| 2005/0090861 A1 | 4/2005 | Porter | |
| 2005/0107886 A1 | 5/2005 | Crabtree et al. | |
| 2005/0123582 A1 | 6/2005 | Sung et al. | |
| 2005/0125051 A1 | 6/2005 | Eidenschink et al. | |
| 2005/0136764 A1 | 6/2005 | Sherman et al. | |
| 2005/0137611 A1 | 6/2005 | Escudero et al. | |
| 2005/0137715 A1 | 6/2005 | Phan et al. | |
| 2005/0159812 A1 | 7/2005 | Dinger, III et al. | |
| 2005/0165128 A1 | 7/2005 | Cohn et al. | |
| 2005/0177144 A1 | 8/2005 | Phan et al. | |
| 2005/0177245 A1 | 8/2005 | Leatherbury et al. | |
| 2005/0182411 A1 | 8/2005 | DeMeo et al. | |
| 2005/0182428 A1 | 8/2005 | Bearinger et al. | |
| 2005/0187602 A1 | 8/2005 | Eidenschink et al. | |
| 2005/0196420 A1 | 9/2005 | Zucherman et al. | |
| 2005/0197422 A1 | 9/2005 | Mayadunne et al. | |
| 2005/0208094 A1 | 9/2005 | Armitage et al. | |
| 2005/0209705 A1 | 9/2005 | Niederauer et al. | |
| 2005/0240281 A1 | 10/2005 | Slivka et al. | |
| 2005/0273106 A1 | 12/2005 | Oepen | |
| 2006/0027612 A1 | 2/2006 | Boaron | |
| 2006/0051394 A1 | 3/2006 | Moore et al. | |
| 2006/0067973 A1 | 3/2006 | Schachter | |
| 2006/0095138 A1* | 5/2006 | Truckai et al. | 623/23.62 |
| 2006/0121084 A1 | 6/2006 | Borden et al. | |
| 2006/0121087 A1 | 6/2006 | Williams et al. | |
| 2006/0136071 A1 | 6/2006 | Maspero et al. | |
| 2006/0149248 A1 | 7/2006 | Schlienger et al. | |
| 2006/0177480 A1 | 8/2006 | Sung et al. | |
| 2006/0178748 A1 | 8/2006 | Dinger, III et al. | |
| 2006/0188546 A1 | 8/2006 | Giroux | |
| 2006/0188547 A1 | 8/2006 | Bezwada | |
| 2006/0200150 A1 | 9/2006 | Ilomaki et al. | |
| 2006/0247610 A1 | 11/2006 | Lanphere et al. | |
| 2006/0263335 A1 | 11/2006 | France et al. | |
| 2006/0264948 A1 | 11/2006 | Williams | |
| 2006/0293749 A1 | 12/2006 | Hudgins et al. | |
| 2007/0005094 A1 | 1/2007 | Eaton et al. | |
| 2007/0014831 A1 | 1/2007 | Sung et al. | |
| 2007/0041950 A1 | 2/2007 | Leatherbury et al. | |
| 2007/0043376 A1 | 2/2007 | Leatherbury et al. | |
| 2007/0043433 A1 | 2/2007 | Chandrasekaran | |
| 2007/0048383 A1 | 3/2007 | Helmus | |
| 2007/0050018 A1 | 3/2007 | Wainwright | |
| 2007/0065652 A1 | 3/2007 | Liebschner | |
| 2007/0067043 A1 | 3/2007 | Dericks | |
| 2007/0083205 A1 | 4/2007 | Attawia et al. | |
| 2007/0100449 A1 | 5/2007 | O'Niel et al. | |
| 2007/0128154 A1 | 6/2007 | Hadba et al. | |
| 2007/0134305 A1 | 6/2007 | Zilberman | |
| 2007/0141111 A1 | 6/2007 | Suokas et al. | |
| 2007/0156251 A1 | 7/2007 | Karmon | |
| 2007/0162019 A1 | 7/2007 | Burns et al. | |
| 2007/0182041 A1 | 8/2007 | Rizk et al. | |
| 2007/0191963 A1 | 8/2007 | Winterbottom et al. | |
| 2007/0213828 A1* | 9/2007 | Trieu et al. | 623/17.11 |
| 2007/0260324 A1 | 11/2007 | Joshi et al. | |
| 2007/0265622 A1 | 11/2007 | Aeschlimann et al. | |
| 2007/0270852 A1 | 11/2007 | Tormala et al. | |
| 2007/0276366 A1 | 11/2007 | Gaines, Jr. | |
| 2007/0280983 A1 | 12/2007 | Strickler et al. | |
| 2007/0299151 A1 | 12/2007 | Gueicher et al. | |
| 2007/0299156 A1 | 12/2007 | Brown et al. | |
| 2007/0299449 A1 | 12/2007 | Allinniemi et al. | |
| 2008/0015578 A1 | 1/2008 | Erickson et al. | |
| 2008/0077140 A1 | 3/2008 | Osman | |
| 2008/0085297 A1 | 4/2008 | Dave et al. | |
| 2008/0086199 A1 | 4/2008 | Dave et al. | |
| 2008/0109037 A1 | 5/2008 | Steiner et al. | |
| 2008/0154368 A1 | 6/2008 | Justis et al. | |

(56) References Cited

U.S. PATENT DOCUMENTS

| | | |
|---|---|---|
| 2008/0154373 A1 | 6/2008 | Protopsaltis et al. |
| 2008/0200638 A1 | 8/2008 | Redepenning |
| 2008/0206297 A1 | 8/2008 | Roeder et al. |
| 2008/0228186 A1 | 9/2008 | Gall et al. |
| 2008/0234754 A1 | 9/2008 | McCarthy et al. |
| 2008/0234762 A1 | 9/2008 | Forstein et al. |
| 2008/0241211 A1 | 10/2008 | Han et al. |
| 2008/0249633 A1 | 10/2008 | Wu |
| 2008/0262613 A1 | 10/2008 | Gogolewski |
| 2008/0305144 A1 | 12/2008 | Brown et al. |
| 2009/0030160 A1* | 1/2009 | Kanazawa et al. ............ 525/450 |
| 2009/0048145 A1 | 2/2009 | Hellerbrand et al. |
| 2009/0093888 A1 | 4/2009 | Dawson et al. |
| 2009/0099600 A1 | 4/2009 | Moore et al. |
| 2009/0149856 A1 | 6/2009 | Paakinaho et al. |
| 2009/0171064 A1 | 7/2009 | Arimura et al. |
| 2009/0204116 A1 | 8/2009 | Shalaby et al. |
| 2009/0270923 A1 | 10/2009 | Tormala et al. |
| 2009/0274742 A1 | 11/2009 | Brown |
| 2010/0136648 A1 | 6/2010 | Balderas et al. |

FOREIGN PATENT DOCUMENTS

| | | |
|---|---|---|
| DE | 1604403 B1 | 11/1970 |
| DE | 2817778 | 11/1978 |
| DE | 2947985 | 9/1981 |
| DE | 3036611 A1 | 6/1982 |
| DE | 3936188 | 5/1990 |
| DE | 4226465 | 2/1993 |
| DE | 4220216 | 1/1994 |
| DE | 102005032005 A1 | 1/2007 |
| EP | 204931 | 12/1986 |
| EP | 299004 | 1/1989 |
| EP | 321389 | 6/1989 |
| EP | 326426 | 8/1989 |
| EP | 404004 | 6/1990 |
| EP | 401844 | 12/1990 |
| EP | 439892 | 8/1991 |
| EP | 475077 | 3/1992 |
| EP | 590656 | 4/1994 |
| EP | 595956 | 5/1994 |
| EP | 326426 B1 | 12/1994 |
| EP | 635274 | 1/1995 |
| EP | 531487 | 1/1996 |
| EP | 711534 | 5/1996 |
| EP | 747072 | 12/1996 |
| EP | 751165 | 1/1997 |
| EP | 803521 | 10/1997 |
| EP | 805175 | 11/1997 |
| EP | 806283 | 11/1997 |
| EP | 1000958 A1 | 5/2000 |
| EP | 1009448 | 6/2000 |
| EP | 1056487 | 12/2000 |
| EP | 1086711 | 3/2001 |
| EP | 1136510 | 9/2001 |
| EP | 1142597 | 10/2001 |
| EP | 1093774 | 6/2002 |
| EP | 1216717 | 6/2002 |
| EP | 1277482 | 1/2003 |
| EP | 815809 | 3/2004 |
| EP | 1284756 | 9/2004 |
| FR | 2691991 | 10/1993 |
| FR | 2691901 | 12/1993 |
| FR | 2863478 A1 | 6/2005 |
| GB | 807589 | 1/1959 |
| GB | 1416575 A | 12/1975 |
| GB | 2215209 | 9/1989 |
| JP | 62-199429 | 9/1987 |
| JP | 01-192367 | 8/1989 |
| JP | 2169612 | 6/1990 |
| JP | 02-270519 | 11/1990 |
| JP | 03-021613 | 1/1991 |
| JP | 05-147105 | 6/1993 |
| JP | 06-065460 | 3/1994 |
| JP | 06-234157 | 8/1994 |
| JP | 8196617 | 8/1996 |
| JP | 9040761 | 2/1997 |
| JP | 9095606 | 4/1997 |
| JP | 9221539 | 8/1997 |
| JP | 9234241 | 9/1997 |
| JP | 09234241 A | 9/1997 |
| JP | 9272790 | 10/1997 |
| JP | 10176039 | 6/1998 |
| JP | 10309313 | 11/1998 |
| JP | 11209595 | 8/1999 |
| JP | 2003-094516 | 4/2003 |
| JP | 2003-518230 | 6/2003 |
| JP | 3503045 | 3/2004 |
| JP | 2006-503172 | 1/2006 |
| JP | 2007046050 | 2/2007 |
| KR | 0180858 | 4/1999 |
| WO | 8404311 | 11/1984 |
| WO | 9003768 | 4/1990 |
| WO | 9301773 | 2/1993 |
| WO | 9534331 | 12/1995 |
| WO | 9622061 A1 | 7/1996 |
| WO | 9705193 | 2/1997 |
| WO | 9725936 | 7/1997 |
| WO | 97/29673 | 8/1997 |
| WO | 9736555 | 10/1997 |
| WO | 9826814 | 6/1998 |
| WO | 9800141 | 7/1998 |
| WO | 9830141 | 7/1998 |
| WO | 9847445 | 10/1998 |
| WO | 9911296 | 3/1999 |
| WO | 9911297 | 3/1999 |
| WO | 9922770 | 5/1999 |
| WO | 0001426 | 1/2000 |
| WO | 00/56376 | 9/2000 |
| WO | 0146501 | 6/2001 |
| WO | 0196105 | 12/2001 |
| WO | 0200137 | 1/2002 |
| WO | 0234159 | 5/2002 |
| WO | 0234310 | 5/2002 |
| WO | 02076725 | 10/2002 |
| WO | 03004071 | 1/2003 |
| WO | WO 03057844 A2 * | 7/2003 |
| WO | 03064531 | 8/2003 |
| WO | 2004011054 | 2/2004 |
| WO | 2004071356 | 8/2004 |
| WO | 2004110313 | 12/2004 |
| WO | 2005014718 | 2/2005 |
| WO | 2005028534 | 3/2005 |
| WO | 2005046470 | 5/2005 |
| WO | 2005085313 | 9/2005 |
| WO | 2008112875 A | 9/2005 |
| WO | 2008112893 A | 9/2005 |
| WO | 2005112804 | 12/2005 |
| WO | 2006053936 | 5/2006 |
| WO | 2006064025 | 6/2006 |
| WO | 2006095138 | 9/2006 |
| WO | 2006108114 | 10/2006 |
| WO | 2006114483 | 11/2006 |
| WO | 2006116129 | 11/2006 |
| WO | 2007020430 | 2/2007 |
| WO | 2007020432 | 2/2007 |
| WO | 2007021593 | 2/2007 |
| WO | WO 2007020430 A2 * | 2/2007 |
| WO | 2007023296 | 3/2007 |
| WO | 2007024492 | 3/2007 |
| WO | 2007020430 A | 4/2007 |
| WO | WO2007038009 A2 | 4/2007 |
| WO | 2007065074 | 6/2007 |
| WO | 2007084609 | 7/2007 |
| WO | 2007086832 | 8/2007 |
| WO | 2007111808 | 10/2007 |
| WO | 2007117499 | 10/2007 |
| WO | 2008001633 | 1/2008 |
| WO | 2008116591 | 3/2008 |
| WO | 2008044011 | 4/2008 |
| WO | 2008044011 | 6/2008 |
| WO | 2008067531 | 6/2008 |
| WO | 2008089172 | 7/2008 |

(56) References Cited

FOREIGN PATENT DOCUMENTS

| WO | 2008098019 | 8/2008 |
| WO | 2008101932 | 8/2008 |
| WO | 2008112912 | 9/2008 |
| WO | 2008131197 | 10/2008 |
| WO | 2008131197 A1 | 10/2008 |
| WO | 2008134264 | 11/2008 |
| WO | 03004071 | 1/2013 |

OTHER PUBLICATIONS

Water Transport in Polylactic Acid (PLA), Siparsky et al. Journal of Environmental Polymer Degradation, vol. 5, No. 3, 1997.*

Andriano, et al., 'Processing and characterization of absorbable polylactide polymers for use in surgical implants,' Journal of Applied Biomaterials, 5(2):133-140 (1994).

Asano, et al., 'In vivo characteristics of low molecular weight copoly(D.L-lactic acid) formulations with controlled release of LH-RH agonist,' Biomaterials, 10(8):569-573 (1989).

Barca, et al., 'Resorbable poly-L-lactic acid mini-staples for the fixation of Akin osteotomies,' The Journal of Foot and Ankle Surgery, 36(2):106-111 (1997).

Bartenev et al.; On the theory of biaxial orientation of amorphous polymers, Mechanics of Composite Materials, 1973, vol. 6, p. 671-677.

Bertrand, et al., Biocompatibility Aspects of New Stent Technology, JACC, 32(3):562-571 (1998).

Celikkaya, et al., 'Poly(DL-lactide)/Poly(ethylene glycol) Copolymer Particles. I. Preparation and Characterization,' Journal of Applied Polymer Science, 61: 1439-1446 (1996).

D. Hull and T. W. Clyne, 'An introduction to composite materials,' Second Edition, Cambridge University Press, Table of Contents, (1996) 8 pages.

D. Wheeler, et al., 'Effect of bioactive glass particle size on osseous regeneration of cancellous defects,' J. Biomed. Materials Research, 41(4):527-533 (1998).

Daniels, et al., 'Mechanical properties of biodegradable polymers and composites proposed for internal fixation of bone,' J. Applied Biomaterials, 1 :57-78 (1990).

Dauner, et al. 'Resorbable continuous-fiber reinforced polymers for osteosynthesis,' J. Materials Science Materials in Medicine, 9: 173-179 (1998).

Eling, et al., 'Biodegradable Materials of Poly(L-Lactic Acid): 1. Melt-Spun and Solution-Spun Fibres,' Polymer, 23:1587-1593 (1982).

Fambri, et al., 'Biodegradable fibres of poly(I-lactic acid) produced by melt spinning,' Polymer, 38:79-85 (1997).

Frenger, 'Biomedical Uses of Shape Memory Polymers,' Biomed. Sci. Instrum., 29:47-50 (1993).

Fukuzaki, et al., Synthesis of copoly(D,L-Lactic acid) with relatively low molecular weight and in vitro degradation, Japan Atomic Energy Research Institute, Gunma, Jpn, European Polymer Journal,25(10):1019-1026 (1989).

Gautier, et al., 'Poly(a-hydroxyacids) for application in the spinal cord: Resorbability and biocompatibility with adult rate Schwann cells and spinal cord,' Journal of Biomedical Materials Research, 42(4):642-654 (1998).

Giardino, et al., 'Experimental evaluation of a resorbable intramedullary plug for cemented total hip replacement,' Biomaterials, 18(13):907-913 (1997).

Gogolewsji, et al., 'Resorbable materials of poly(L-lactide). II Fibers spun from solutions of poly(L-lactide) in good solvents,' J. Appl. Polymer Sci., 28:1045-1061 (1983).

Grijpma et al., 'Chain Entanglement Mechanical Properties and Drawability of Poly (Lactide),' Colloid Polym Sci., 272:1068-1081 (1994).

Haers, et al., 'Biodegradable polyactide plates and screws in orthognathic surgery,' Technical Note, Journal of Cranio-Maxillofacial Surgery, 26(2):87-91 (1998).

Hyon, et al., 'Effects of residual monomer on the degradation of DL-lactide polymer,' Hyon, Jamshidi & Ikeda, Polymer International, 46:196-202 (1998).

J. West et al, 'Bioactive Polymers, Synthetic biodegradable polymer scaffolds,' Chapter 5, pp. 83-95, Anthony Atala and David J. Mooney, Editors; Joseph P. Vacanti and Robert Langer, Associate Editors, Birkhauser (1997).

Kaitian, et al., 'Poly(D,L-Lactic Acid) Homopolymers: Synthesis and Characterization,' Turkish Journal of Chemistry, 20:43-53 (1996).

Kister, et al., 'Effects of morphology, conformation and configuration on the IR and Raman spectra of various poly(lactic acid)s,' Polymer, 39(2): 267-273 (1998).

Koelling, et al., 'In vitro real-time aging and characterization of poly(L/D-lactic acid),' Proceedings of the 1997 1fth Southern Biomedical Engineering Conference (Cat. No. 97TH8270), pp. 197-201.

Kontio, et al., 'Fibrous wound repair associated with biodegradable poly-L/D-lactide copolymers implants: study of the expression of tenascin and cellular fibronectin,' Journal of Materials Science-Materials in Medicine, 9:10:603-609 (1988).

Kricheldorf, et al., 'Polyactones: 32. High-molecular weight polylactides by ring-opening polymerization with dibutylmagnesium or butylmagnesium chloride,' Polymer, 36(15):2995-3003 (1995).

L. L. Hench, 'Bioactive materials: The potential for tissue regeneration,' J. Biomed. Materials Research, 41(4):511-518 (1998).

Losken, et al., 'Memory of DL-polylactic acid biodegradable plates,' Ann. Plast. Surg., 32(6):606-611 (1994).

MacDonald, et al., 'Enzymatic degradability of poly(lactide): Effects of chain stereochemistry and material crystallinity,' Macromolecules, 29(23):7356-7361 (1996).

Mainil-Varlet, et al., 'Effect of in vivo and in vitro degradation on molecular and mechanical properties of various low-molecular weight polylactides,' Journal of Biomedical Materials Research, 36(3):360-380 (1997).

Matsumura, et al., 'Novel ring opening polymerization of lactide by lipase,' Macromol. Symp., 130:285-304 (1998).

Mauduit, J. et al.; "Hydrolytic degradation of films prepared from blends of high and low molecular weight poly (DL lactic acid)s" Journal of Biomedical Materials Research, 1996, vol. 30, p. 201-207.

Morita, et al., 'Intravitreous delivery of dexamethasone sodium m-sulfobenzoate from poly(DL-lactic acid)implants,' Biological & Pharmaceutical Bulletin, 21 (2): 188-190 (1998).

Okihara, et al., Crystal structure of stereocomplex of poly(L-lactide) and poly(D-lactide), Journal of Macromolecular Science-Physics, B30(1 and 2): 119-140 (1991).

Okuzaki, et al., Mechanical Properties and Structure of the Zone-Drawn Poly(I-lactic acid) Fibers, Journal of Polymer Science, Part B, Polymer Physics, 37:991-996 (1999).

Oriented Polymer Materials, Edited by Stoyko Fakirov, published by Huthig & Wepf Verlag Zug, Heidelberg, Oxford CTIUSA, Table of Contents pp. v, viii, ix-xix (1996).

Penning, et al., 'Preparation and properties of absorbable fibres from I-lactide copolymers,' Polymer, 34(5):942-951 (1993).

Pitt, et al., 'Modification of the rates of chain cleavage of polY(e-caprolactone) and related polyesters in the solid state,' Journal of Controlled Release, 4:283-292 (1987).

Pitto, et al., "Comparison of fixation of the femoral component without cement and fixation with use of a bone-vacuum cementing technique for the prevention of fat embolism during total hip arthroplasty," J. Bone Joint Surg., 81-A(6)~831-843 (1999).

Rak, et al., 'The preparation and characterization of poly(D,L-lactic acid) for use as a biodegradable drug carrier,' (1985) liverpool Poly tech., liverpool, UK, Pharmaceutica Acta Helvetiae, 60:(5-6):162-169.

Ristic, et al., 'An investigation of synthesis and degradation of poly(D,L-lactide) and controlled release of albumin from biodegradable poly(D,L-lactide) cylinders,' ICheaP-2, the second Italian conference on chemical and process engineering, Florence, pp. 559-563 (1995).

Schliephake, et al., 'Reconstruction of the mandible by prefabricated autogenous bone grafts,' Int. J. Oral Maxillofac. Surg., 26:244-252 (1997).

(56) References Cited

OTHER PUBLICATIONS

Stahelin, et al., Clinical degradation and biocompatibility of different bioabsorbable interference screws: a report of six cases: Arthroscopy: The Journal of Arthroscopic & Related Surgery, 13(2):238-244 (1997).
Steendam, et al., The role of elastic relaxation in drug delivery from poly(DL-lactic acid) based tablets. A shape memory phenomenon: Proceedings of the International Symposium on Controlled Release of Bioactive Materials, 25:128-129 (1998).
Stevels, et al., 'Blends van blok copolymeren die een poly(L-lactide) of poly(D-lactide) blok bevatten,' Biomedical Science and Engineering Meeting, pp. 107-110 (1994).
Tagl, "Thesis—The morselized and impacted bone graft animal experiments on proteins, impaction and load," Acta Orthop. Scand. Suppl., 290:1-40 (2000).
Temenoff et al., "Injectable biodegradable materials for orthopedic tissue engineering," Biomaterials, 21:2405-2412 (2000).
Tschakaloff, et al., 'Degradation kinetics of biodegradable DL-polyactic acid biodegradable implants depending on the site of implantation,' International Journal of Oral and Maxillofacial Surgery, 23(6 Pt2):443-445 (1994).
Zegzula, et al., 'Bone Formation with Use of rhBMP-2 (Recombinant Human Bone Morphogenetic Protein-2,' The Journal of Bone and Joint Surgery, 79:1778-1790 (1997).
Zhang, Biodegradable lactide polymers: synthesis, degradation, and controlled drug release properties (drug release), Queen's University at Kingston, Canada, vol. 55/01-B of Dissertation Abstracts International, p. i-xv, 1-179 (Oct. 1993).
Office Action for Japanese Application No. 2010504268 dated Jul. 17, 2012, 6 pages.
Office Action for Japanese Application No. 2010504268 dated Jan. 8, 2013, 4 pages.
Japanese Office Action dated Jun. 19, 2012 for JP Application 2010-504182. p. 1-6.
Examination Report for counterpart Australian Application No. 2008242737 dated Aug. 10, 2012, pp. 1-3.
Atkins, G., Haynes, D.R., Howie, D.W., & Findlay, D.M., Role of polyethylene particles in peri-prosthetic osteolysis: A Review, World of Journals of Orthopedics, 2(10), Oct. 18, 2011, pp. 93-101.
Hill, R.G., "Biomedical Polymers: Biomaterials, artificial organs and tissue engineering", Imperial College London, UK, date unknown but prior to the date of this application, 7 pages.
Vert, M., Li, S.M., Spenlehaur, G., Guerin, P., "Pioresorbability and biocompatibility of aliphatic polyesters", Journal of Materials Science: Materials in Medicine 3, 1992, pp. 432-446.
English Translation, Decision to Reject the Amendments, and Decision of Rejection for Japanese Patent Application No. 2010-504268 dated Oct. 1, 2013, 11 pages.
Steendam, et al. The role of elastic relaxation in drug delivery from poly(DL-lactic acid) based tablets. A shape memory phenomenon: Proceedings of the International Symposium on Controlled Release of Bioactive Materials, 25:128-129 (1998).
Stevels, et al., "Blends can clok copolumeren die een poly(L-lactide) of poly(D-ladtide) blok bevatten", Biomedical Science and Engineering Meeting, pp. 107-110 (1994).
Structure and Properties of Oriented Polymers, Ed. I. M. Ward, Department of Physics, University of Leads, England, a Halsted Press Book, John Wiley & Sons, New York-Toronto (1975) Table of Contents.
Summary of the Office Action, dated Mar. 19, 2012, 1 page.
Tagl, "These—The morselized and impacted bone graft animal experiments on proteins, impaction and load", Acta Orthop. Scan. Suppl., 290:1-40 (2000).
Temenoff, et al., "Injectable biodegradable materials for orthopedic tissue engineering", Biomaterials, 21:2405-2412 (2000).
Tschakaloff, et al., "Degradation kinetics of biodegradable DL-polyactic acid biodegradable implants depending on the site of implantation", International Journal of Oral and Maxillofacial Surgery, 23(6):443-445 (1994).

Tsuji, et al., Stereocomplex formation between enantiomeric poly(lactic acid). VIII. Complex Fibers spun from mixed solution of poly(D-lactic acid) and poly(L-lactic acid), Journal of Applied Polymer Science, 51(2):337-344 (1994).
West, J., "Bioactive Polymers, Synthetic biodegradable polymer scaffolds", Chapter 5, pp. 83-95, Anthony Atala and David J. Mooney, Editors; Joseph P. Vacanti and Robert Langer, Associate Editors, Birkhauser (1997).
Zegula, et al. "Bone Formation with Use of rhBMP-2 (Recombinant Human Bone Morphogenetic Protein-2", The Journal of Bone and Joint Surgery, 79:1778-1790 (1997).
Zhang, Biodegradable lactide polmers: synthesis, degradation, and controlled drug release properties (drug release), Queen's University at Kingston, canada, vol. 55/01-B of Dissertation Abstracts International, p. i-xv, 1-179 (Oct. 1993).
International Search Report and Written Opinion for PCT/US2008/060783 dated Jul. 23, 2008.
International Preliminary Report on Patentability and Written Opinion for PCT Application No. PCT/GB2012/052478 dated Apr. 8, 2014, 14 pages.
International Search Report for PCT Application No. PCT/GB2012/052478 dated Jun. 20, 2013, 5 pages.
International Preliminary Report on Patentability and Written Opinion for PCT Application No. dated Apr. 8, 2014, 6 pages.
International Search Report for PCT Patent Application No. PCT/GB2012/052470 dated Feb. 22, 2013, 2 pages.
International Search Report for PCT Application No. PCT/GB2012/052475 dated Mar. 8, 2013, 3 pages.
International Search Report and Written Opinion for PCT Application No. PCT/GB2012/052475 dated Apr. 8, 2014, 10 pages.
International Preliminary Report on Patentability and Written Opinion for PCT Application No. PCT/GB2012/052480 dated Apr. 8, 2014, 12 pages.
International Search Report for PCT Application No. PCT/GB2012/052480 dated May 31, 2013, 4 pages.
International Search Report and Written Opinion for PCT/US2008/060783 dated Jul. 23, 2008, 2 pages.
Andriano et al., "Processing and characterization of absorbable polyactide polymers for use in surgical implants", Journal of Applied Biomaterials, 5(2):133-140 (1994).
Barca et al., "Resorbable poly-L-lactic acid in mini-staples of the fixation of Akin osteotomies", The Journal of Foot and Ankle Surgery, 36(2)106-111 (1997).
Bartenev et al., On the theory of biaxial orientation of amorphous polymers, Mechanics of Composite Materials, 1973, co. 6, p. 671-677.
Bertrand et al., "Biocompatibility Aspects of New Stent Technology", JACC, 32(3):562-571 (1998).
Celikkaya et al., "Poly(DL-lactide)Poly(ethylene glycol) Copolymer Particles. I preparation and Characterization", Journal of Applied Polymer Science, 61:1439-1446 (1996).
D. Hull and T.W. Clyne, "An introduction to composite materials," Second Edition, Cambridge University Press, Table of Contents, (1996), 8 pages.
D. Wheeler et al., "Effect of bioactive glass particle size on osseous regeneration of cancellous defects", J. Biomed. Materials Research, 41(4):527-533 (1998).
Daniels et al., "Mechanical properties of biodegrabable polymers and compisites proposed for internal fixation of bone, "J. Applied Biomaterials, 1:57-78 (1990).
Dauner et al., "Resorbable continuous-fiber polymers for osteosynthesis", J Materials Science Materials in Medicine, 9:173-179 (1998).
Eling, et al., "Biodegradable Materials of poly(I-lactic acid):1. Melt-Spun and Solution-Spun Fibres", Polymer, 23:1587-1593 (1982).
Farnbri, et al., "Biodegradable fibres of poly(I-lactic acid) produced by melt spinning", Polymer, 38: 79-85 (1997).
First Japanese Office Action for Application No. 2010-503579 dated Mar. 6, 2012, 6 pages.
First Office Action for Patent Application No. JP 2010-504201, mail dated Mar. 19, 2013, 5 pages.
Frenger, "Biomedical Uses of Shape Memory Polymers", Miomed. Sci. Instrum., 29:47-50 (1993).

(56) References Cited

OTHER PUBLICATIONS

Fukuzaki et al., Synthesis of copoly(D, L-Lactic acid) with relatively low molecular weight and in vitro degradation, Japan Atomic Energy Research Institute, Gunma, Jpn, European Polymer Journal, 25(10):1019-1026 (1989).
Gautier et al., "Synthesis of copoly(a-hydroxyacids) for application in the spinal cord: Resorbability and biocompatibility with adult rate Schwann cells and spinal cord", Journal of Biomedican materials Research, 42(4):642-654 (1998).
Giardino et al., "Experiemental evaluation of a resorbable intramedullary plug for cemented total hip replacement", Biomaterials, 18(13)907-913 (1997).
Gogolewski et al., "Resorbable materials of poly(L-lactide). II Fibers spun from solutions of poly(L-lactide) in good solvents", J Appl. Polymer Sci., 28:1045-1061, (1983).
Grijpma et al., "Chain Entanglement Mechanical Properties and Drawability of Poly (Lactide)", Colloid Polym Sci., 272:1068-1081 (1994).
Haers et al., "Biodegradable polyactide plates and screws in othognathic surgery", Technical Note, Journal of Cranio-Maxillofacial Surgery, 26(2):87-91 (1998).
Hench, L.L., "Bioactive materials: The potential for tissue regeneration", J. Biomed. Materials Research, 41(4):511-518 (1998).
Hyon et al., "Effects of residual monomer on the degradation of DL-lactide polymer", Hyon, Jamshidi & Ikada, Polymer International, 46:196-202 (1998).
International Search Report and Written Opinion for PCT/GB2008/001331 dated Aug. 25, 2008.
International Search Report and Written Opinion for PCT/US2008/060401 dated Jan. 9, 2009.
Kaitian, et al., "Poly(D,L-lactic Acid) Homopolymers: Synthesis and characterization", Turkish Journal of Chemistry, 20:43-53 (1996).
Kister, et al., "Effects of morphology, conformation and configuration on the IR and Raman spectra of various poly (lactic acid)s", 39(2):267-273 (1998).
Koelling, et al., "In vitro real-time aging and characterization of poly(L/D-lactic acid)", Proceedings of the 1997 1ffh Southern Biomedical Engineering Conference (Cat. No. 97TH8270), pp. 197-201.
Kontio, et al., "Fibrous wound repair associated with biodegradable poly-L/D-lactide copolymers implants: study of the expression of tenascin and cellular fibronectin", Journal of Materials Science—Materials in Medicine, 9:10:603-609 (1988).
Kricheldorf, et al., "Polyactones: 32. High-molecular weight polyactides by ring-opening polymerization with dibutylmagnesuim or butylmagnesium chloride", Polymer, 36(15):2995-3003 (1995).
Losken, et al., "Memory of DL-polylacitc acid biodegradable plates", Ann. Plast. Surg., 32(6):606-611 (1994).
MacDonald, et al., "Enzymatic degradability of poly(lactide): Effects of chain stereochemistry and material crystallinity", Macromolecules, 29(23):7356-7361 (1996).
Mainil-Varlet, et al. "Effect on in vitro degradation on molecular and mechanical properties of various low-molecular weight polulactides", Journal of Biomedical Research, 36(3):360-380 (1997).
Matsumura, et al., "Novel ring opening polymerization of lactide by lipase", Macromol. Symp., 130:285-304 (1998).

Mauduit, et al., "Hydrolytic degradation of films prepared from blends of high and low molecular weight poly (DL lactic acid)s" Journal of Biomedical Materials Research, 1996, vol. 30, p. 201-207.
Mitsura Momma, et al., "Long Bone Intramedullary Fixation Method Using Shape Memory Anchoring Nails—An Attempt at a Biomechanical Test And The Application Thereof to Proximal Humeral Fractures," Journal of the Eastern Japan Association of Orthopaedics and Traumatology, vol. 12, No. 4, pp. 385-390 and back cover, 2000, 8 pages.
Morita, et al., "Intravitreous delivery of dexamethasone sodium m-sulfobnenzoate from poly(DL-lactic acid) implants", Biological & Pharmaceutical Bulletin, 21(2):188-190 (1998).
Notice of Reasons for Rejection for Japanese Patent Application No. 2010-504201 dated Nov. 26, 2013, 10 pages and English Translation thereof.
Ofer Nativ, et al. "Bladder Neck Suspension Using Bone Anchors for the Treatment of Female Stress Incontinence," ASAIO Journal, vol. 43, No. 3, pp. 204-208 and cover, May-Jun. 1997, 6 pages.
Okihara, et al., Crystal structure of stereocomplex of poly(D-lactide), Journal of Macomolecular Science-Physics, B30 (1 and 2):119-140 (1991).
Okuzaki, et al., Mechanical Properties and Structure of the Zone-Drawn Poly(L-lactic acid) Fibers, Journal of Polymer Science, Part B, Polymer Physics, 37:991-996 (1999).
Oriented Polymer Materials, edited by Stoyko Fakirov, published by Huthig & Wepf Verlag Zug, Heidelberg, Oxford CTIUSSA, Table of Contents pp. v, viii, ix-xix (1996).
PCT/GB2008/001331 International Preliminary Report on Patentability with Written Opinion dated Oct. 20, 2009, 8 pages.
Penning, et al. "Preparation and properties of absorbable fibres from I-lactide copolymers", Polymer, 34(5):942-951 (1993).
Pitt, et al. "Modification of the rates of chain cleavage of Poly(e-caprolactone) and related polyesters in the solid state", Journal of Controlled Release, 4:283-292 (1987).
Pitto, et al., "Comparison of finxation of the femoral componenet without cement and fixation with use of a bone-vaccuum cementing technique for the prevention of fat embolism during total hip anthroplasty", J. Bone Joint Surg., 81A(6):831-843 (1999).
Rak et al., "The preparation and characterization fo poly(D,L-lactic acid) for use as a biodegradable drug carrier", (1985) liverpool Poly tech, liverpool UK, Pharmaceutica Acta Hevetiae, 60:(5-6):162-169.
Ristic et al., "An investigation of synthesis and degradation of poly(D,L-lactide) and controlled release of albumin from biodegradable poly (D,L-lactide) cylinders," IcheaP-2, the second Italian conference on chemical procedures and process engineering, Florence, pp. 559-563 (1995).
Schliephake, et al., "Reconstruction on the mandible by prefabricated autogenous bone grafts", Int. J. Oral Maxillofacial. Surg., 26:244-252 (1997).
Second Japanese Office Action for Application No. 2010-503579 dated Feb. 19, 2013, 3 pages.
Stahelin, et al. Clinical degradation and biocompatibility of different bioabsorbable interference screw: a report of six cases: Arthroscopy: The Journal of Arthroscopic & Related Surgery, 13(2):238-244 (1997).

\* cited by examiner

MULTI-MODAL SHAPE MEMORY POLYMERS

CROSS-REFERENCE TO RELATED APPLICATIONS

This application is a U.S. National Stage Application, submitted under 35 U.S.C. 371, claiming priority to PCT International Patent Application PCT/US2008/060783 filed on Apr. 18, 2008, which claims priority to U.S. Patent Application No. 60/912,827 filed on Apr. 19, 2007, the disclosures of which are incorporated herein by reference in their entirety.

BACKGROUND

1. Field of the Invention

This present disclosure relates generally to shape memory polymers and, more particularly, multi-modal shape memory polymers.

2. Related Art

Amorphous orientated shape memory polymers containing single molecular weight distributions are known to relax and form fixation devices when placed into a bone cavity. Upon observation, these shape memory polymer materials relax and try to flow into the small pores of bone. Polymers used for current shape memory applications have molecular weight distributions of polydispersity in the range of between about 2 to about 4. These types of ranges may limit the ability of the polymer to penetrate into the bone, the mechanical properties of the polymer itself, or in the case where the polymer is resorbable, the degradation time of the polymers.

SUMMARY

In an aspect, the present disclosure relates to a multi-modal shape memory polymer material comprising a blend of at least one polymer component having a first molecular weight and at least a second polymer component having a second molecular weight that is less than the first component. In an embodiment, the polymer material is bi-modal. In another embodiment, the first molecular weight has an $M_n$ in excess of about 30,000 Daltons and the second molecular weight has an $M_n$ of up to about 30,000 Daltons. In yet another embodiment, the first molecular weight has an $M_n$ of between about 50,000 and about 1,000,000 Daltons and the second molecular weight has an $M_n$ of between about 2,000 and about 30,000 Daltons. In a further embodiment, the at least one polymer component comprises about 80% of the polymer blend and the second polymer component comprises about 20% of the polymer blend.

In an embodiment, the at least one polymer component and the second polymer component are both resorbable. In another embodiment, the at least one polymer component and the second polymer component are both non-resorbable. In yet another embodiment, one of the at least one polymer component and the second polymer component is resorbable and one of the at least one polymer component and the second polymer component is non-resorbable. In a further embodiment, both of the components are miscible. In yet a further embodiment, the material includes a filler selected from a group consisting essentially of hydroxyapatite, calcium carbonate, and tricalcium phosphate.

In an embodiment, the material includes a porogen selected from a group consisting essentially of sodium chloride, lithium bromide, lithium iodide, calcium chloride, sodium iodide, magnesium sulphate, and calcium sulphate. In another embodiment, at least one or both of the at least one polymer component and the second polymer component includes a polyester selected from a group including P(L)LA, poly(D)lactic acid (P(D)LA), poly(DL)lactic acid (P(DL)LA), poly(L-co-DL)lactic acid (P(LDL)LA), poly(L)lactic acid-co-glycolide (P(L)LGA)), poly(DL)lactic acid-co-glycolide (P(DL)LGA)), poly(D)lactic acid-co-glycolide (P(D)LGA)), polycaprolactone (PCL), PGA, and combinations thereof.

In yet another embodiment, at least one or both of the at least one polymer component and the second polymer component includes a polyacrylate. In a further embodiment, at least one or both of the at least one polymer component and the second polymer component includes a polymethyl methacrylate polymer or copolymer thereof. In yet a further embodiment, at least one or both of the at least one polymer component and the second polymer component includes a polybutyl methacrylate polymer or copolymer thereof. In an embodiment, at least one or both of the at least one polymer component and the second polymer component includes a polybutyl methacrylate-co-polymethyl methacrylate copolymer. In another embodiment, at least one or both of the at least one polymer component and the second polymer component includes a polystyrene copolymer.

In another aspect, the present disclosure relates to an article comprising a multi-modal shape memory polymer material comprising a blend of at least one polymer component having a first molecular weight and at least a second polymer component having a second molecular weight that is less than the first component. The article is selected from a group consisting essentially of rods, pins, nails, screws, plates, anchors, and wedges.

In a further aspect, the present disclosure relates to the use of the article as a fixation device suitable for implantation into bone wherein upon implanting the article into bone and providing the article with energy, the material flows into pores of the bone thereby enhancing fixation of the article to bone.

In yet a further aspect, the present disclosure relates to an article comprising a multi-modal shape memory polymer material comprising a blend of at least one polymer component having a first molecular weight and at least a second polymer component having a second molecular weight that is less than the first component, wherein upon implanting the article into bone and providing the article with energy, the material flows into pores of the bone thereby enhancing fixation of the article to bone.

Further features, aspects, and advantages of the present disclosure, as well as the structure and operation of various embodiments of the present disclosure, are described in detail below with reference to the accompanying drawings.

BRIEF DESCRIPTION OF THE DRAWINGS

The accompanying drawings, which are incorporated in and form a part of the specification, illustrate the embodiments of the present disclosure and together with the description, serve to explain the principles of the disclosure. In the drawings.

DETAILED DESCRIPTION OF THE EMBODIMENTS

Figure 1:
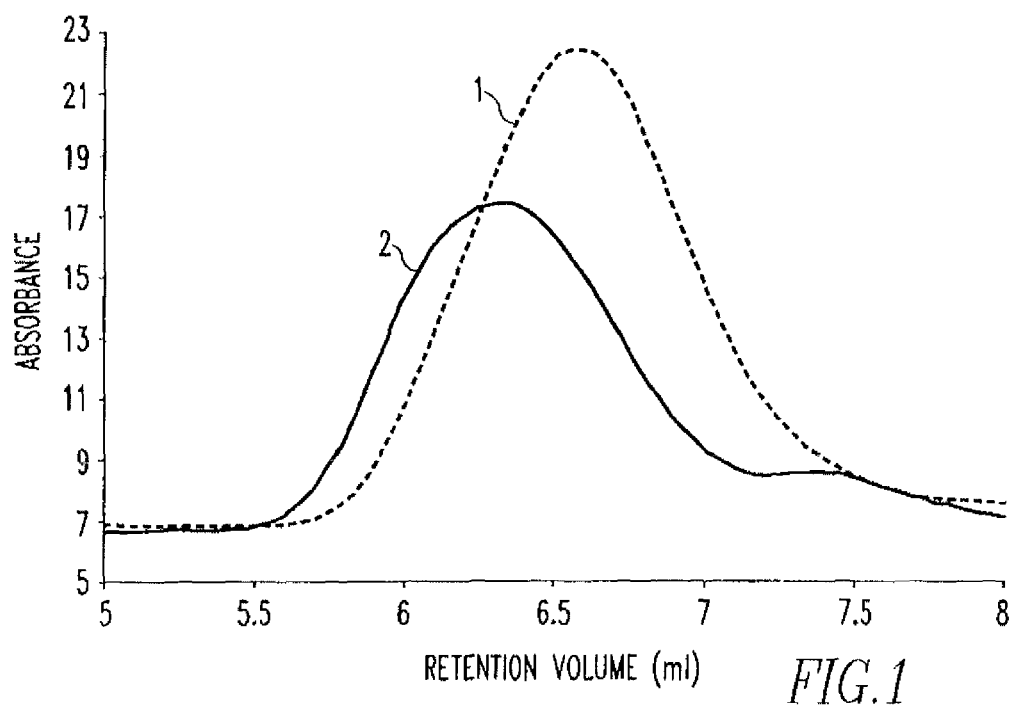
FIG. 1 is an overlayed chromatograph showing the molecular weight profile distribution of a monomodal polymer material and the multi-modal polymer material of the present disclosure.

The following description of the preferred embodiments) is merely exemplary in nature and is in no way intended to limit the disclosure, its application, or uses.

The present disclosure relates to a multi-modal shape memory polymer material comprising a blend of at least one polymer component having a first molecular weight and at least a second polymer component having a second molecular weight that is less than the first component.

The first polymer component represents about 80% of the polymer blend and includes a high molecular weight having an $M_n$ in excess of about 30,000 Daltons, and in some embodiments, between about 50,000 and about 1,000,000 Dollops. The second component represents about 20% of the polymer blend and includes a low molecular weight having an $M_n$ of up to about 30,000 Daltons, and in some embodiments, between about 2,000 and about 30,000 Daltons. The high molecular weight of the first component provides the blend with the necessary mechanical strength and the low molecular weight of the second component provides the blend with the necessary flow characteristics and therefore the necessary amount of integration of the blend into bone, as will be further described below.

For the purposes of this disclosure, both the first and second polymer components include a polylactide based shape memory polymer. However, the polymer material may include a resorbable and/or non-resorbable polymer material having shape-memory qualities and which is selected from a group that includes an amorphous polymer, a semi-crystalline polymer, and combinations thereof.

Specific polymers that may be used include polyacrylic/polyacrylate, polymethyl methacrylate (PMMA), polyethyl methacrylate (PEMA), polybutylacrylate, polybutylmethacrylate, polystyrene, poly-alpha-hydroxy acids, polycaprolactones, polydioxanones, polyesters, polyglycolic acid, polyglycols, polylactides, polyorthoesters, polyphosphates, polyoxaesters, polyphosphoesters, polyphosphonates, polysaccharides, polytyrosine carbonates, polyurethanes, and copolymers or polymer blends thereof. Also, the polymer components may be miscible and capable of forming a substantially uniform blend. Polyesters that may be used include P(L)LA, poly(D)lactic acid (P(D)LA), poly(DL)lactic acid (P(DL)LA), poly(L-co-DL)lactic acid (P(LDL)LA), poly(L)lactic acid-co-glycolide (P(L)LGA)), poly(DL)lactic acid-co-glycolide (P(DL)LGA)), poly(D)lactic acid-co-glycolide (P(D)LGA)), polycaprolactone (PCL), PGA, and combinations thereof.

Generally, polymers that display shape memory qualities show a large change in modulus of elasticity at the glass transition temperature ($T_g$). The shape-memory function can be achieved by taking advantage of this characteristic. Namely, the mixture of the first and second polymer components is processed, via processes known to one of skill in the art, to make an article having a definite shape (the original shape). The article is then processed to give the article a secondary shape and to provide the article with shape memory qualities The process may process include, without limitation, die drawing, zone drawing, hydrostatic extrusion, compression flow molding, thermoforming, rolling, and roll drawing. The article is then softened by providing the article with energy and heating to a temperature ($T_f$) higher than the $T_g$ of the polymer, but lower than the melting temperature ($T_m$) thereof so as to deform the article back to its original shape.

The article may include fixation devices, such as, without limitation, rods, pins, intramedullary nails, bone screws, locking screws, plates, anchors, staples, and wedges, for use in the repair of bone and soft tissue. In addition, the article may include a sleeve of polymer material, including a central channel, which allows the sleeve to be placed on a fixation device, such as the fixation devices listed above, for subsequent use in fixating the fixation device to bone, as is described in PCT International Application Publication WO2008/112875, the disclosure of which is incorporated herein by reference in its entirety.

Examples of adding energy to the polymer material include electrical and thermal energy sources, the use of force, or mechanical energy, and/or a solvent. The thermal energy source may include a heated liquid, such as water or saline. It is also within the scope of this disclosure that once the macroscopic body is placed in the bone, body heat would be transferred from blood and tissue, via thermal conduction, to provide the energy necessary to deform the shape memory polymer material. In this instance, body temperature would be used as the thermal energy source. Examples of electrical energy sources include heat generating devices such as a cauterizing device or insulated conductor, as more fully described in the '828 application, or a heating probe, as more fully described in PCT International Application Publication WO2008/112880, the disclosure of which is incorporated herein by reference in its entirety.

Any suitable force that can be applied either preoperatively or intra-operatively can be used. One example includes the use of ultra sonic devices, which can relax the polymer material with minimal heat generation. Solvents that could be used include organic-based solvents and aqueous-based solvents, including body fluids. Care should be taken that the selected solvent is not contra indicated for the patient, particularly when the solvent is used intra-operatively. The choice of solvents will also be selected based upon the material to be relaxed. Examples of solvents that can be used to relax the polymer material include alcohols, glycols, glycol ethers, oils, fatty acids, acetates, acetylenes, ketones, aromatic hydrocarbon solvents, and chlorinated solvents.

The article may include a composite or matrix having reinforcing material or phases such as glass fibers, carbon fibers, polymeric fibers, ceramic fibers, ceramic particulates, rods, platelets, and fillers. The fillers may include osteoconductive materials and/or biological actives such as, without limitation, hydroxyapatite, calcium carbonate, and tricalcium phosphate. Other reinforcing material or phases known to one of ordinary skill in the art may also be used. In addition, the polymeric material may be made porous via the use of porogens. The porogens include, without limitation, sodium chloride, lithium bromide, lithium iodide, calcium chloride, sodium iodide, magnesium sulphate, and calcium sulphate. Porosity may allow infiltration by cells from surrounding tissues, thereby enhancing the integration of the material to the tissue.

Also, one or more active agents may be incorporated into the material. Suitable active agents include bone morphogenic proteins, antibiotics, anti-inflammatories, angiogenic factors, osteogenic factors, monobutyrin, thrombin, modified proteins, platelet rich plasma/solution, platelet poor plasma/solution, bone marrow aspirate, and any cells sourced from flora or fauna, such as living cells, preserved cells, dormant cells, and dead cells. It will be appreciated that other bioactive agents known to one of ordinary skill in the art may also be used. Preferably, the active agent is incorporated into the polymeric shape memory material, to be released during the relaxation or degradation of the polymer material. Advantageously, the incorporation of an active agent can act to combat infection at the site of implantation and/or to promote new tissue growth.

EXAMPLE

A bimodal polymer blend, as described above, was prepared by compounding a mixture containing 35% w/w CaCO3, 6.5% w/w Poly(DL-Lactide) (MLA) (molecular weight, $M_n$=13900, $M_w$=20500) and 58.5% w/w Poly(L-co-DL-Lactide) 70:30 (PLDLA) (molecular weight, $M_n$=354700, $M_w$=854500) using a twin screw extruder. The resulting material was moulded to produce a 30 mm diameter rod suitable for die drawing. The rod was drawn through a 15 mm die at 75° C. at a rate of 20 mm/minute to produce a rod with a diameter of about 15 mm. The rod included shape memory qualities. The resulting rod was machined to produce plugs of 25 mm in length and 13 mm in diameter. Each plug also included an 8 mm diameter central opening. A stainless steel sleeve having a 4 mm diameter central opening was then press fitted into the central opening of each plug. The sleeve had a length of 25 mm and a diameter of 13 mm.

A monomodal polymer blend, to be used for control purposes, was prepared by compounding a mixture containing 35% w/w CaCO3, 65% w/w Poly(L-co-DL-Lactide) 70:30 (PLDLA) (molecular weight, $M_n$=354700, $M_w$=854500) using a twin screw extruder. The resulting material was molded to produce a 30 mm diameter rod suitable for die drawing. The rod was drawn through a 15 mm die at 75° C. at a rate of 20 mm/minute to produce a rod with a diameter of approximately 15 mm. The rod included shape memory qualities. Each plug also included an 8 mm diameter central opening. A stainless steel sleeve having a 4 mm diameter central opening was then press fitted into the central opening of each plug. The sleeve had a length of 25 mm and a diameter of 13 mm.

The molecular weight of both the monomodal and the bimodal polymer blends was determined using gel permeation chromatography (GPC). Table 1 provides the molecular weights of the monomodal and bimodal polymer plugs.

TABLE 1

| Material | Molecular weight (Mn) | Molecular weight (Mw) | Polydisperity (Mw/Mn) |
|---|---|---|---|
| Monmodal | 97200 | 244700 | 2.6 |
| Bimodal | 101200 | 426700 | 4.2 |

Figure 2:
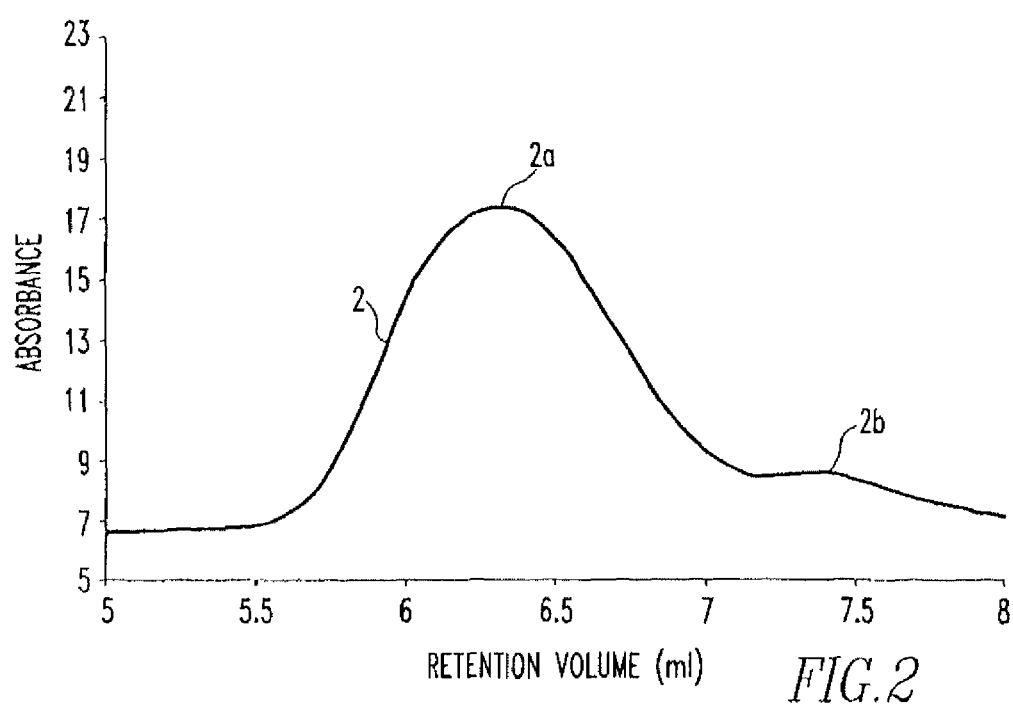
FIG. 2 is a chromatograph showing the molecular weight profile distribution of the multi-modal polymer material of the present disclosure.

Additionally, FIGS. 1 and 2 show the molecular weight profile distributions of the monmodal and the bimodal polymer plugs. Specifically, FIG. 1 is an overlayed chromatograph showing graphs 1,2 for both the monomodal polymer plug and the bimodal polymer plug, respectively, and FIG. 2 is a chromatograph showing only the graph 2 for the bimodal polymer plug. The first peak 2a represents the high molecular weight PLLA-co-DL material and the second peak 2b represents the low molecular weight MLA material.

Samples of the monomodal and the bimodal plugs, described above, were placed into 14 mm diameter sawbone cavities. Each plug was heated for 15 min at 175° C. using a 4 mm diameter heating probe. In order to heat the plugs, the probe was inserted into the central opening of the stainless steel rods. The plugs were then allowed to cool after which the fixation force was measured using the following procedure:

Each sample of sawbone was placed on a cylindrical support on an Instron 5566 test machine. A rigid metal probe of 8 mm diameter, connected rigidly to a 10 kN load cell, was pressed against the one end of each of the plugs at 2 mm/min. The maximum force to push out the plug in each case was recorded and is shown in Table 2 below.

TABLE 2

| | Push out force (N) |
|---|---|
| Bimodal plug | |
| 1 | 2148 |
| 2 | 2265 |
| 3 | 2880 |
| Mean | 2431 (+/−393) |
| Monomodal plug | |
| | 375 |
| | 460 |
| Mean | 417 (+/−43) |

Hence it can be concluded that a multi-modal polymer composition having shape memory qualities contains substantially enhanced mechanical properties compared to a monomodal shape memory polymer composition. It is believed that the enhanced mechanical properties are due to the combination of the high strength high molecular weight polymer and the flow characteristics of the low molecular weight polymer. Specifically, due to the miscibility of the polymer components, it is believed that the lower molecular weight polymer component plasticizes the higher molecular weight component. This aids flow of the multi-modal material into pores of the bone, and hence, fixation of the plug to the bone, thereby providing the plug with enhanced mechanical properties.

For the purposes of this disclosure, a multi-modal polymer composition is a polymer composition having more than one molecular weight distribution. The multi-modal composition used in this disclosure has two molecular weight distributions (bimodal), however, polymer compositions having more than two molecular weight distributions are also within the scope of this disclosure. In addition, although for the purposes of this disclosure the low molecular weight component is present at about 20% and the high molecular weight component is present at about 80%, the components may be present in any suitable proportions to give the desired increase in strength and flowability. Furthermore, the polymer blend of the present disclosure may be present as a homopolymer blend or as a co-polymer blend.

In view of the foregoing, it will be seen that the several advantages of the disclosure are achieved and attained.

The embodiments were chosen and described in order to best explain the principles of the disclosure and its practical application to thereby enable others skilled in the art to best utilize the disclosure in various embodiments and with various modifications as are suited to the particular use contemplated.

As various modifications could be made in the constructions and methods herein described and illustrated without departing from the scope of the disclosure, it is intended that all matter contained in the foregoing description or shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A bone implantation article comprising a multi-modal shape memory polymer material comprising a blend of at least a first polymer component having a first molecular weight and at least a second polymer component having a second molecular weight that is less than the first component, the first polymer component and the second polymer component are miscible, at least one of the first or second polymer components are non-resorbable, and wherein upon implanting the article into bone and providing the article with energy and heating to a temperature higher than the glass transition temperature of the polymer, but lower than its melting temperature, the material flows into pores of the bone thereby enhancing fixation of the article to bone.

2. The article of claim 1, wherein the first molecular weight is in excess of about 50,000 Daltons and the second molecular weight is up to about 20,000 Daltons.

3. The article of claim 1, wherein the first molecular weight is between about 50,000 and about 1,000,000 Daltons and the second molecular weight is between about 2,000 and about 20,000 Daltons.

4. The article of claim 1, wherein the first polymer component comprises about 80% of the polymer blend and the second polymer component comprises about 20% of the polymer blend.

5. The article of claim 2, wherein the first polymer component comprises about 80% of the polymer blend and the second polymer component comprises about 20% of the polymer blend.

6. The article of claim 1, wherein the first polymer component and the second polymer component are both non-resorbable.

7. The article of claim 1, wherein one of the first polymer component and the second polymer component is resorbable and one of the first polymer component and the second polymer component is non-resorbable.

8. The article of claim 1, wherein the material comprises reinforced polymeric material comprising a composite or matrix including reinforcing material or phases selected from the group consisting of glass fibers, carbon fibers, polymeric fibers, ceramic particualtes, rods, and platelets.

9. The article of claim 1, wherein the material is porous.

10. The article of claim 1, wherein the material comprises active agents selected from the group consisting of bone morphogenic proteins, antibiotics, anti-inflammatories, angiogenic factors, osteogenic factors, monobutyrin, thrombin, modified proteins, platelet rich plasma, platelet rich solution, platelet poor plasma, platelet poor solution, and bone marrow aspirate.

11. The article of claim 10, wherein the active agent is incorporated into the polymeric shape memory material to be released during the relaxation and/or degradation of the polymer material.

12. The article of claim 10, wherein the active agent combats infection and/or promotes new tissue growth at the site of implantation.

13. The article of claim 1, wherein at least one of the first or second polymer components is selected from the group consisting of polylyacrylate, polymethyl methacrylate polymer or copolymer thereof, polybutyl methacrylate polymer or copolymer thereof, and polystyrene copolymer.

* * * * *